(12) United States Patent
Althaus

(10) Patent No.: US 6,440,747 B2
(45) Date of Patent: Aug. 27, 2002

US006440747B2

(54) STABILIZATION OF BIOLOGICAL FLUIDS BY ADDITION OF STEROL ESTERS

(75) Inventor: Harald Althaus, Wetter (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/429,475

(22) Filed: Oct. 29, 1999

(51) Int. Cl.$^7$ ............... G01N 1/00; G01N 31/00
(52) U.S. Cl. ............... 436/176; 436/8; 436/13; 436/16; 436/18; 436/71
(58) Field of Search ............... 436/8, 13, 15, 436/16, 17, 18, 63, 71, 174, 176

(56) References Cited

U.S. PATENT DOCUMENTS

| | | | | |
|---|---|---|---|---|
| 4,011,045 A | * | 3/1977 | Bonderman | 436/13 |
| 4,045,176 A | * | 8/1977 | Proksch et al. | 436/13 |
| 4,184,848 A | * | 1/1980 | Batz et al. | 436/175 |
| 4,189,400 A | * | 2/1980 | Proksch et al. | 436/13 |
| 4,282,001 A | * | 8/1981 | Klose et al. | 436/174 |
| 4,503,146 A | * | 3/1985 | Yun et al. | 435/19 |
| 4,579,825 A | * | 4/1986 | Siedel et al. | 436/175 |
| 4,626,511 A | * | 12/1986 | Artiss et al. | 436/8 |
| 4,649,120 A | | 3/1987 | Steuer et al. | 436/13 |
| 4,716,119 A | | 12/1987 | Rehner et al. | 436/16 |

FOREIGN PATENT DOCUMENTS

| | | |
|---|---|---|
| DE | 31 07 060 | 9/1982 |
| DE | 33 29 952 | 2/1985 |
| WO | 93/00807 | * 1/1993 |

OTHER PUBLICATIONS

Beyer et al., "Steroide," Lehrbuch der organische Chemie, S. 649–664, 1981.

* cited by examiner

*Primary Examiner*—Maureen M. Wallenhorst
(74) *Attorney, Agent, or Firm*—Finnegan, Henderson, Farabow, Garrett and Dunner, L.L.P.

(57) ABSTRACT

The present invention relates to the use of sterol esters for the long-term stabilization of biological fluids, in particular even those which are obtained by lyophilization and subsequent reconstitution.

21 Claims, No Drawings

STABILIZATION OF BIOLOGICAL FLUIDS BY ADDITION OF STEROL ESTERS

The present invention relates to the use of sterol esters for the long-term stabilization of biological fluids, in particular even those which are obtained by lyophilization and subsequent reconstitution.

In all studies with biological fluids, in particular in those on which or with the aid of which investigations which are to be assessed optically are to be carried out, the problem of turbidity poses itself. The cause of this turbidity is not always detectable, often it is precipitation of protein or lipid from the solution. Additionally held responsible for these instabilities are the lipoprotein macromolecules occurring in body fluids, which on account of their content of water-insoluble phospholipids have a tendency to aggregate per se.

If labile protein solutions are stored, the development of turbidity, or adsorption of the proteins on vessel walls can likewise occur, which considerably impairs the quality of these products.

The abovementioned instabilities are additionally increased if the biological fluids are lyophilized for stabilization. Examples of biological fluids are serum, plasma, cerebrospinal fluid, pleural exudates or ascites of human or animal origin.

Within the meaning of the invention, such biological fluids can also be solutions of synthetic composition formed from an artificial or alternatively natural liquid matrix (e.g. serum or phosphate-buffered NaCl solution) known per se to the person skilled in the art and added biological substances, which for their part can be prepared by genetic engineering.

Such solutions of synthetic composition are often used as control or standard sera.

Control sera are understood as meaning sera of human or animal origin having an optionally modified, but serum-like composition, which contain serum constituents, for example proteins, enzymes, enzymatically determinable substrates and electrolytes in a known concentration and are suitable for the control of determination methods for these serum constituents.

In order to guarantee the shelf life of labile components such as, for example, enzymes or lipoproteins, biological fluids can be stored in lyophilized form and/or at low temperature, preferentially below −18° C. Undesired side effects of lyophilization are turbidities which occur after reconstitution of the control sera due to alteration of the solubility behavior, especially of the lipoproteins. These turbidities often interfere in spectrophotometric methods so that, for example, a sample blank value is additionally necessary.

Since problems often occur due to turbidity, numerous attempts at elimination have also already been undertaken. Even if solutions have already been found, these, however, were until now essentially restricted to closely defined application areas and conditions.

DE-P 31 07 060 describes the addition of organic non-sugar-like substances such as methanol, alanine, triethylene glycol, valine, acetate, lactate or sodium 2-hydroxymethylbutyrate. Such an addition can result, e.g. in the case of alanine and methylbutyrate, in disturbances of enzyme reactions.

Addition of methanol is generally injurious to health. If sodium acetate is used, the control serum can no longer be employed as a universal control serum for electrolyte determinations. Addition of ammonium compounds interferes with urea determinations. Other substances can cause general test disturbances.

A further process for the avoidance of turbidities by addition of proline and Na desoxycholate has previously been described in DE-A 33 29 952. This addition, however, has the disadvantage that it leads, for example, to artefacts during protein separation and makes difficult deproteination with trichloroacetic acid, e.g. in the determination of creatinine.

The present invention was therefore based on the object of finding a process which can be generally used for the long-term stabilization of biological fluids.

Surprisingly, it was possible by addition of sterol esters to biological body fluids to achieve a stabilization even in the presence of lipoproteins. Even after lyophilization of treated lipoprotein-containing body fluids with sterol esters, a clear product is obtained after dissolution.

Surprisingly, it was also found that labile protein solutions, which tend to become turbid or whose proteins adsorb easily on vessel walls, are stabilized by addition of sterol esters.

Surprisingly, it has furthermore been found that lower turbidity, more homogeneous reconstituted control sera are prepared in particular if sterol ester is added to the control serum before lyophilization. As a result, the serum is on the whole not only more homogeneous but also the precision of concentration and activity determinations of the parameters contained in the control serum is improved, i.e the regaining of the declared theoretical values is facilitated for the user of quality control sera.

Sterol esters belong to the steroids class of substances (gonan derivatives) which generally identifies a hydroxyl group in the 3 β position. Significant differences exist in the side chain attached in the 17(20) position. Sterols are a large class (BEYER et al. (1981), Lehrbuch der organischen Chemie [Textbook of Organic Chemistry], pp. 649–664 "Steroids"). The experiments carried out with different representatives of this class (e.g. vitamin D3, estrone, cholesterol and stigmasterol) show that general applicability is guaranteed. The derivatives of cholesterol are particularly advantageous.

The sterol esters according to the invention moreover have a polyethylene glycol group coupled via a dicarboxylic acid. In principle, all known dicarboxylic acids can be used, since the bifunctional reactivity is essentially decisive for the function according to the invention. The following dicarboxylic acids can advantageously be used: succinic acid, adipic acid, sebacic acid.

The PEG group should fundamentally also guarantee the solubility of the sterol ester, so that the person skilled in the art, if appropriate by means of an experiment, can easily determine the optimum length. According to experience, the following chain lengths are advantageous: polyethylene glycol 600, polyethylene glycol 900 or polyethylene glycol 3000.

The turbidity behavior measured in a nephelometric measuring process advantageously serves as a measure of the stabilizing effect. For the person skilled in the art, it is easy with the aid of the present invention to employ another, corresponding process.

The invention thus relates to a process for the stabilization of biological fluids and the fluids stabilized in this way.

Preferred here is the use, for the long-term stabilization of biological fluids, of sterol esters of the general formula I

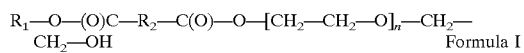

Formula I in which n=1–200 and $R_1$=sterol $R_2$=aliphatic or aromatic ring having 4 to 8 C atoms, of which at least one can be replaced by N, S or O, or is a linear or branched chain having 0 to 12 C atoms, particularly preferred is use of the sterol esters in which $R_1$ is a compound of the general formula II:

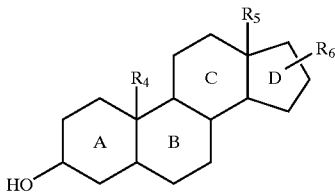

Formula II $R_4$ and $R_5$ can be H or —$CH_3$ $R_6$ can be a straight-chain or branched chain having 1 to 12 C atoms, an —OH or =O group, the rings A, B, C and D can each be saturated, unsaturated or aromatic per se and, if $R_4$=—C(19)$H_3$, the ring B between C(9) and C(10) can be opened with formation of a double bond between C(9) and C(19).

Very particularly preferred is the use of sterol esters, the sterol radical originating from cholesterol, vitamin D3, stigmasterol or estrone.

Advantageously, the sterol ester is added in such a concentration that the concentration in the biological fluid is 0.05–5% by weight, preferentially 0.1–3% by weight, particularly preferentially 0.5–1.5% by weight.

Preferentially, the biological fluid is lyophilized according to a process known per se to the person skilled in the art and reconstituted for use.

The biological fluid can also be frozen until use, advantageously stored at $\leq$-18° C.

The invention also relates to a reagent, essentially consisting of a natural or artificial matrix, at least one diagnostically relevant substance (analyte) and a sterol ester of the general formula I in a concentration of 0.05 to 5% by weight.

To obtain the effect according to the invention, the sterol esters according to the invention can also be combined with the known stabilizers, in particular with detergents.

Particularly advantageous here are combinations of sterol esters with nonionic and/or zwitterionic detergents. The sterol ester concentration in such combinations can advantageously be lowered.

Biological fluids within the meaning of this invention have already been described further above.

The concept of long-term stability is also dependent, inter alia, on the measuring process and the analyte. Fundamentally, the stability, however, should be at least 6 months, preferentially at least 12 months, particularly preferentially at least 18 months. A biological fluid is described as stable within the meaning of the present invention if the turbidity measured at 546 nm has increased by no more than 300% compared with the turbidity of the starting fluid.

The following examples illustrate the invention without restricting it.

EXAMPLE 1

Citrate plasma from a healthy donor was treated with various concentrations of cholesterol-PEG 900 (FLUKA CH-9471 Buchs/Switzerland, Item No. 26735) (CP) and then lyophilized according to processes known per se to the person skilled in the art.

For documentation of the turbidity, after reconstitution of the lyophilizate the blank value was measured on a Behring nephelometer (BNA, Dade Behring Marburg GmbH, D-35001 Marburg/Germany) and the extinction was measured at 546 nm.

|  | Extinction 546 nm | Blank value BNA in bit |
|---|---|---|
| Starting material: Citrate plasma (without addition) | 0.131 | 11 |
|  | 1.151 | >3500 |
| +0.2% CP | 0.643 | 3257 |
| +0.5% CP | 0.643 | 683 |
| +1% CP | 0.165 | 84 |

EXAMPLE 2

Human serum was treated with various concentrations of cholesterol-PEG 900 (CP) and stored at various temperatures (2–8° C., -20° C.) or lyophilized.

For documentation of the turbidity, the blank value was measured on a Behring nephelometer (BNA) and the extinction was measured at 546 nm.

|  | Human serum, untreated | | Human serum + 1% CF | |
|---|---|---|---|---|
|  | Extinction 546 nm | Blank value BNA in bit | Extinction 546 nm | Blank value BNA in bit |
| Starting values | 0.131 | 98 | 0.130 | 98 |
| 4 days at 2–8° C. | 0.215 | 952 | 0.152 | 132 |
| 4 days -20° C. | 0.235 | 581 | 0.171 | 155 |
| 1 year at -20° C. | 0.790 | >3500 | 0.279 | 1837 |
| Lyophilizate (stored at 2–8° C. for 1 year) after reconstitution | 1.630 | >3500 | 0.355 | 1676 |

What is claimed is:

1. A method of producing a stabilized biological fluid, comprising adding to a biological fluid at least one sterol ester of formula I:

$R_1$—O—(O)C—$R_2$—C(O)—O—(CH$_2$—CH$_2$—O)$_n$—CH$_2$—
CH$_2$—OH                                                        Formula I wherein n=1–200;

$R_1$ = a sterol; and $R_2$ is an aliphatic or aromatic ring having from 4 to 8 carbon atoms, wherein one or more of the ring carbon atoms is optionally replaced by N, S, or O, or is a linear aliphatic carbon chain having from 0 to 12 carbon atoms, or is a branched aliphatic carbon chain having from 0 to 12 carbon atoms, wherein 0 carbon atoms represents a bond;

wherein the sterol ester is added to the biological fluid in a concentration of from 0.05% to 5% by weight; and wherein for a period of between 12 and 18 months after addition of the sterol ester to the biological fluid, the biological fluid has a turbidity measured at 546 nanometers that is increased by no more than 300% compared with the turbidity of the biological fluid before addition of the sterol ester.

2. The method as claimed in claim 1, wherein $R_1$ is a sterol of formula II:

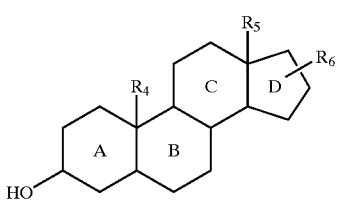

Formula II wherein $R_4$ is H or —$CH_3$;

$R_5$ is H or —$CH_3$;

$R_6$ is selected from a linear carbon chain having from 1 to 12 carbon atoms, a branched carbon chain having from 1 to 12 carbon atoms, an —OH group, and a =O group; and the rings A, B, C and D are each independently saturated, unsaturated, or aromatic.

3. The method as claimed in claim 2, wherein $R_4$=—$C(19)H_3$; and the ring B between C(9) and C(10), is optionally opened and a double bond is formed between C(9) and C(19).

4. The method as claimed in claim 3, further comprising lyophilizing and reconstituting the stabilized biological fluid for use.

5. The method as claimed in claim 2, further comprising lyophilizing and reconstituting the stabilized biological fluid for use.

6. The method as claimed in claim 1, wherein $R_1$ is selected from cholesterol, vitamin D3, stigmasterol, and estrone.

7. The method as claimed in claim 6, further comprising lyophilizing and reconstituting the stabilized biological fluid for use.

8. The method as claimed in claim 1, further comprising lyophilizing and reconstituting the stabilized biological fluid for use.

9. The method as claimed in any one of claims 1 to 6, further comprising freezing the stabilized biological fluid until use.

10. The method of claim 9, wherein the frozen stabilized biological fluid is stored at $\leq -18°$ C.

11. The method as claimed in claim 1, wherein the biological fluid is stabilized for a period of at least 18 months.

12. The method as claimed in claim 1, wherein for a period of between 12 and 18 months after addition of the sterol ester to the biological fluid, the biological fluid has a turbidity measured at 546 nanometers that is increased by no more than 300% compared with the turbidity of the biological fluid immediately after addition of the sterol ester.

13. A composition of matter, comprising a natural or artificial matrix;

at least one substance to be analyzed; and at least one sterol ester of Formula I:

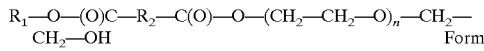

Formula I in a concentration of 0.05 to 5% by weight, wherein n=1–200;

$R_1$=a sterol; and $R_2$ is an aliphatic or aromatic ring having from 4 to 8 carbon atoms, wherein one or more of the ring carbon atoms is optionally replaced by N, S, or O, or is a linear aliphatic carbon chain having from 0 to 12 carbon atoms, or is a branched aliphatic carbon chain having from 0 to 12 carbon atoms, wherein 0 carbon atoms represents a bond; and wherein for a period of between 12 and 18 months after preparing the composition, the composition has a turbidity measured at 546 nanometers that is increased by no more than 300% compared with a composition that lacks the at least one sterol ester but is otherwise identical.

14. The composition as claimed in claim 13, wherein the concentration is from 0.1 to 3% by weight.

15. The composition as claimed in claim 13, wherein the concentration is from 0.5 to 1.5% by weight.

16. The composition as claimed in claim 13, wherein the natural or artificial matrix is an artificial matrix.

17. The composition as claimed in claim 16, wherein the artificial matrix comprises a phosphate-buffered NaCl solution.

18. The composition as claimed in claimed 13, wherein for a period of between 12 and 18 months after addition of the sterol ester to the composition, the composition has a turbidity measured at 546 nanometers that is increased by no more than 300% compared with the turbidity of-the composition immediately after addition of the sterol ester.

19. A method of producing a stabilized artificial matrix, comprising adding to an artificial matrix at least one sterol ester of formula I:

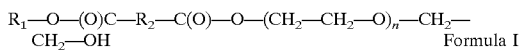

Formula I wherein n=1–200;

$R_1$=a sterol; and $R_2$ is an aliphatic or aromatic ring having from 4 to 8 carbon atoms, wherein one or more of the ring carbon atoms is optionally replaced by N, S, or O, or is a linear aliphatic carbon chain having from 0 to 12 carbon atoms, or is a branched aliphatic carbon chain having from 0 to 12 carbon atoms, wherein 0 carbon atoms represents a bond;

wherein the sterol ester is added to the artificial matrix in a concentration of from 0.05% to 5% by weight; and wherein for a period of between 12 and 18 months after addition of the sterol ester to the artificial matrix, the artificial matrix has a turbidity measured at 546 nanometers that is increased by no more than 300% compared with the turbidity of the artificial matrix before addition of the sterol ester.

20. The method as claimed in claim 19, wherein the artificial matrix comprises a phosphate-buffered NaCl solution.

21. The method as claimed in claim 19, wherein for a period of between 12 and 18 months after addition of the sterol ester to the artificial matrix, the artificial matrix has a turbidity measured at 546 nanometers that is increased by no more than 300% compared with the turbidity of the artificial matrix immediately after addition of the sterol ester.

* * * * *

UNITED STATES PATENT AND TRADEMARK OFFICE
CERTIFICATE OF CORRECTION

PATENT NO. : 6,440,747 B2
DATED : August 27, 2002
INVENTOR(S) : Harald Althaus

It is certified that error appears in the above-identified patent and that said Letters Patent is hereby corrected as shown below:

Title page,
After Item [22], "Filed: Oct. 29, 1999", insert the following missing data:

-- [30] Foreign Application Priority Data
Oct. 30, 1998         (DE) ................ 198 50 074 --.

Column 5,
Line 28, after "C(10)", delete the comma.
Line 45, "any one of claims 1 to 6," should read -- any one of claims 1, 2, 3, or 6, --.

Column 6,
Line 25, "in claimed 13," should read -- in claim 13, --.
Line 29, "of-the" should read -- of the --.

Signed and Sealed this

Twenty-second Day of April, 2003

JAMES E. ROGAN
*Director of the United States Patent and Trademark Office*